United States Patent [19]

Boltralik

[11] Patent Number: 4,686,214

[45] Date of Patent: Aug. 11, 1987

[54] ANTI-INFLAMMATORY COMPOUNDS FOR OPHTHALMIC USE

[75] Inventor: John J. Boltralik, Fort Worth, Tex.

[73] Assignee: Alcon Laboratories, Inc., Fort Worth, Tex.

[21] Appl. No.: 792,992

[22] Filed: Oct. 30, 1985

[51] Int. Cl.$^4$ .............................................. A61K 31/56
[52] U.S. Cl. .................................... 514/179; 514/177; 514/178; 514/180; 514/181; 514/914
[58] Field of Search ............. 260/397.3, 397.4, 397.45; 514/177, 178, 179, 180, 181, 914

[56] References Cited

U.S. PATENT DOCUMENTS

| | | | |
|---|---|---|---|
| 3,007,923 | 11/1961 | Muller et al. | 260/239.55 |
| 3,862,194 | 1/1975 | Woods et al. | 260/397.45 |
| 3,947,478 | 3/1976 | Woods et al. | 260/397.3 |
| 4,472,392 | 9/1984 | Anderson et al. | 424/243 |
| 4,472,393 | 9/1984 | Shapiro | 424/243 |
| 4,477,445 | 10/1984 | Philibert et al. | 424/239 |

OTHER PUBLICATIONS

Phillips et al, "Eye Drops of RU 486-6, A Peripheral Steroid Blocker, Lower Intraocular Pressure in Rabbits", *The Lancet*, vol. 1, No 8380 (1984).

Rousseau, et al, "17β-Carboxamide Steroids are a New Class of Glucocorticoid Antagonists", *Nature*, vol. 279 (1979).

Chemical Abstracts; vol. 96 (1982); #35625s; Cairns et al.

*Primary Examiner*—Douglas W. Robinson
*Attorney, Agent, or Firm*—James A. Arno; Gregg C. Brown

[57] ABSTRACT

Anti-inflammatory compounds and a method of treating inflamed ocular tissue utilizing these compounds are described. The steroidal actives are advantageously characterized in that they do not cause any significant increase in intraocular pressure during chronic use.

2 Claims, No Drawings

ANTI-INFLAMMATORY COMPOUNDS FOR OPHTHALMIC USE

BACKGROUND OF THE INVENTION

1. Field of the Invention

The present invention relates to the treatment of ophthalmic inflammatory disorders with a class of steroids which does not adversely affect intraocular pressure.

2. Discussion of Related Art

Anti-inflammatory steroids, such as, hydrocortisone, prednisolone, dexamethasone, and fluorometholone, are very useful in controlling a wide range of ophthalmic inflammatory conditions. However, this indication is not without risk of an induced side effect associated with the chronic use of these compounds. This side effect may be manifested by a rise in intraocular pressure (IOP) in steroid responders.

The above-described manifestations can generally be tolerated in most patients over a relatively short treatment period, such as, four to six weeks or less. However, the increase in IOP caused by these compounds is generally unacceptable over extended periods of treatment, such as one to twelve months or more. The increased intraocular pressure associated with the short term use of these compounds may also be unacceptable in certain patients, such as, patients already suffering from an elevated IOP (e.g., glaucoma patients). Therefore, a need exists for anti-inflammatory compounds suitable fo ophthalmic use which do not cause any significant increase in IOP, and for a method of treating ophthalmic inflammatory disorders utilizing such compounds.

SUMMARY OF THE INVENTION

A principal object of the present invention is the provision of pharmaceutical compositions and methods of using such compositions in treating ophthalmic inflammatory disorders which does not result in any significant increase in IOP, or in fact stabilizes or lowers IOP; wherein the method comprises applying said compositions comprising an effective amount of a compound of Structure (I), below, to the affected eye(s) when indicated for the relief of inflammation:

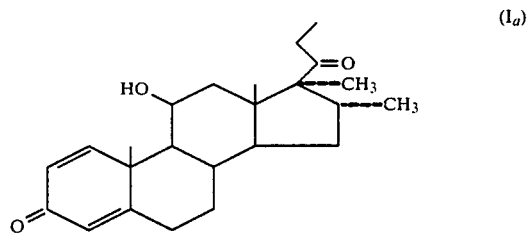

wherein:
X = a member of the group consisting of H and halogen;
Y = a member of the group consisting of $H_2$, H(OH), H(Acyl) and O;
$R^1$ = a member of the group consisting of H, $CH_3$ and halogen;
$R^2$ = alkyl having 1–4 carbon atoms;
$R^3$ = a member of the group consisting of H, OACYL, OALKYL, AND $CH_3$;
$R^4$ = a member of the group consisting of H and alkyl having 1–4 carbon atoms; and
$C_1$–$C_2$ and $C_6$–$C_7$ are selected from a saturated and an unsaturated bond.

DETAILED DESCRIPTION OF THE INVENTION

The compounds of the present invention are defined by Structure (I) above. These compounds are fully disclosed in U.S. Pat. No. 3,947,478, which also discloses their anti-inflammatory dermatological utility. This patent is fully incorporated herein by reference to the extent that it defines the compounds of Structure (I) and how to make them. While the anti-inflammatory utility of these compounds as dermatologicals is known, there is no disclosure indicating ophthalmic utility, i.e., that the compounds of Structure (I) have anti-inflammatory activity in the eye and that their use does not adversely affect IOP. In this regard the art has long searched for a steroid or class of steroids which would meet the following features of the steroids of Structure (I): 1. Ophthalmic anti-inflammatory activity; 2. Capable of topical delivery; and 3. Does not raise IOP.

The following species member of the genus defined by Structure (I) is especially preferred:

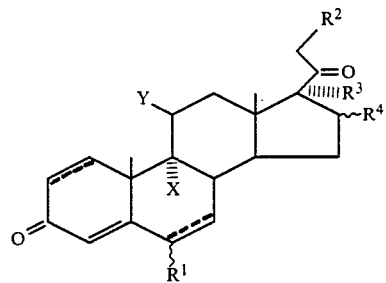

The compounds of Structure (I) may be incorporated into various types of ophthalmic formulations for delivery to the eye. For example, these compounds may be combined with ophthalmologically acceptable preservatives, surfactants, viscosity enhancers, buffers, sodium chloride and water to form an aqueous, sterile ophthalmic suspension. In order to prepare sterile ophthalmic ointment formulations, the active ingredient is combined with a preservative in an appropriate vehicle, such as, mineral oil, liquid lanolin or, white petrolatum. Sterile ophthalmic gel formulations may be prepared by suspending the active ingredient in a hydrophilic base prepared from the combination of Carbopol-940 (a carboxy vinyl polymer available from the B. F. Goodrich Company) according to published formulations for analogous ophthalmic preparations; preservatives and tonicity agents can be incorporated. The specific type of formulation selected will depend on various factors, such as, the type of inflammation being treated (e.g., internal or external), and dosage frequency. Ophthalmic suspensions, ointments and gels are the preferred dosage forms. The compounds will normally be contained in these formulations in an amount of 0.05% to 2.0% by weight. Thus, for topical presentation these formulations would be delivered in modest excess to the surface of the eye 1–3 times/day depending upon the discretion of the clinician. While preservatives are normally recommended for multidose containers, their presence is not critical. Pharmaceutical compositions of the present invention designed for single use do not require any preservative.

Intracameral delivery is also contemplated by the present invention, for example, during surgery. Typically, such intracameral formulations would contain from 0.0001% to 0.01% by weight of a compound of Structure (I) in an aqueous vehicle, for example, a dispersion in HEALON (Pharmacie). Details of the use of such compositions delivered intracamerally by injection or during surgery, would be left to the discretion of the clinician and would be indicated to combat internal uveal tract inflammations.

EXAMPLE 1

The formulations set out below illustrate the dosage forms which may be utilized in the present invention. In these formulations, the term "steroid" represents any of the above-described compounds of Structure (I), specifically including the compound of Structure (Ia).

|  | Composition % W/W |
|---|---|
| Suspension | |
| Steroid | 0.05–2.0 |
| Benzalkonium Chloride | 0.001–0.02 |
| Polysorbate-80 or Tyloxopol | 0.01–1.0 |
| Phosphate buffer pH | 5 mMol–100 mMol |
| Sodium Chloride | 0–0.9 |
| Hydroxypropyl methylcellulose | 0.1–0.5 |
| Water to produce 100 parts by weight | |
| Ointment | |
| Steroid | 0.05–2.0 |
| Chlorobutanol | 0.5 |
| Methyl or propyl parabens | 0.01–0.1 |
| Mineral Oil | 0–10 |
| Liquid Lanolin | 0–10 |
| White petrolatum to product 100 parts by weight | |
| Gel | |
| Steroid | 0.05–2.0 |
| Carbopol-940 | 1–4 |
| Sodium hydroxide | q.s. (pH: 4.5–8.0) |
| Sodium chloride | 0–0.9 |
| Water q.s. | |

The treatment method of the present invention comprises applying an anti-inflammatory effective amount of a compound of Structure (I) to the affected ocular tissue when indicated for the relief of inflammation. The dosage regimen utilized will depend on various factors, such as, the severity of the inflammation and the duration of action of the particular formulation utilized. In general, the above-described formulations may be topically applied, for example, as drops to the upper globe, or as a 0.5–1 cm strip of ointment or gel to the lower conjunctival sac of the eye. Suspensions will generally be applied 2 to 4 times daily, while ointments or gels will generally be applied once or twice daily. The application of sustained release formulations (e.g., polymer based gels) once daily at bedtime will be preferred in some conditions.

The above described formulations are useful in treating virtually any type of ocular inflammation. These formulations are especially useful in the treatment of ocular inflammation in patients who are predisposed to experiencing elevated intraocular pressure when treated with a conventional steroid compound; this class of patients, which is estimated as consituting approximately 5% of the general population, is referred to as "steroid responders". The formulations also have special value in treating ocular inflammation in patients suffering from open angle glaucoma, since it has been estimated that approximately 92% of these patients experience a large increase in intraocular pressure after chronic (i.e., 6 to 8 weeks) steroid therapy. Finally, the formulations also find special use in treating the inflamed ocular tissue of patients who are predisposed to open-angle glaucoma or ocular hypertension.

The present invention has been described above in connection with certain preferred embodiments. However, as obvious variations thereon will become apparent to those skilled in the art, the invention is not to be considered as limited thereto. The invention is only limited by the claims which follow.

What is claimed is:

1. A method of treating ocular inflammation which comprises applying to the eye an anti-inflammatory effective amount of a compound of the following structure:

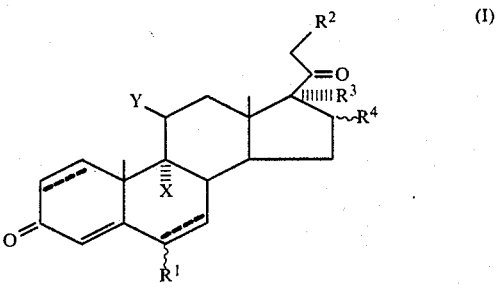

wherein:
X = a member of the group consisting of H and halogen;
Y = a member of the group consisting of $H_2$ H(OH), H(OAcyl) and O;
$R^1$ = a member of the group consisting of H, $CH_3$ and halogen;
$R^2$ = alkyl having 1–4 carbon atoms;
$R^3$ = a member of the group consisting of H, OAcyl, Oalkyl, and $CH_3$;
$R^4$ = a member of the group consisting of H and alkyl having 1–4 carbon atoms; and $C_1$–$C_2$ and $C_6$–$C_7$ are selected from a saturated and an unsaturated bond.

2. A method according to claim 1 wherein the compound is:

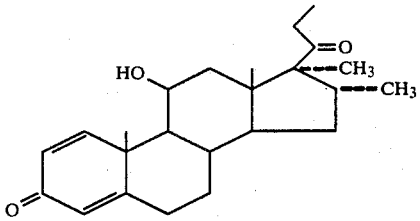

* * * * *